United States Patent
Nagasawa et al.

(10) Patent No.: US 9,481,870 B2
(45) Date of Patent: Nov. 1, 2016

(54) NUCLEIC ACID ENCODING A POLYPEPTIDE HAVING AMINOTRANSFERASE ACTIVITY, VECTORS AND HOST CELLS COMPRISING THE NUCLEIC ACID

(75) Inventors: Toru Nagasawa, Nagoya (JP); Toyokazu Yoshida, Gifu (JP); Kouichi Ishida, Gifu (JP); Noriyuki Ito, Takasago (JP); Shigeru Kawano, Takasago (JP); Yoshihiko Yasohara, Takasago (JP)

(73) Assignee: KANEKA CORPORATION, Osaka (JP)

( * ) Notice: Subject to any disclaimer, the term of this patent is extended or adjusted under 35 U.S.C. 154(b) by 74 days.

(21) Appl. No.: 13/876,400

(22) PCT Filed: Sep. 28, 2011

(86) PCT No.: PCT/JP2011/072171
§ 371 (c)(1),
(2), (4) Date: Mar. 27, 2013

(87) PCT Pub. No.: WO2012/043622
PCT Pub. Date: Apr. 5, 2012

(65) Prior Publication Data
US 2013/0210092 A1 Aug. 15, 2013

(30) Foreign Application Priority Data
Sep. 28, 2010 (JP) .................... 2010-216547

(51) Int. Cl.
| | |
|---|---|
| C07H 21/00 | (2006.01) |
| C12N 1/21 | (2006.01) |
| C12N 1/19 | (2006.01) |
| C12P 17/00 | (2006.01) |
| C12P 41/00 | (2006.01) |
| C12N 1/15 | (2006.01) |
| C12N 9/10 | (2006.01) |
| C12P 17/10 | (2006.01) |

(52) U.S. Cl.
CPC ............ *C12N 9/1096* (2013.01); *C12P 17/10* (2013.01); *C12P 41/006* (2013.01); *C12Y 206/01* (2013.01); *Y02P 20/52* (2015.11)

(58) Field of Classification Search
CPC . C12N 9/1096; C12Y 206/01; C12P 41/006; C12P 17/10
See application file for complete search history.

(56) References Cited

U.S. PATENT DOCUMENTS

| | | | |
|---|---|---|---|
| 7,622,302 B1 | 11/2009 | Barton et al. | |
| 2010/0285544 A1 | 11/2010 | Ito et al. | |

FOREIGN PATENT DOCUMENTS

| | | | |
|---|---|---|---|
| JP | 2007-185133 | * | 7/2006 |
| JP | 2006-523447 A | | 10/2006 |
| WO | WO 2006/126498 | | 11/2006 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Yamamoto et al., GenBank accession No. DJ063479, Jan. 23, 2008.*
Ausubel, F., Current Protocols in Molecular Biology, Hybridization Analysis of DNA Blots, pp. 2.10.8-2.10.11.*
Guo et al., PNAS 101(25):9205-9210, 2004.*
Database DDBJ/EMBL/GenBank [online], Accession No. AF124929, <http://www.ncbi/nlm.nih/giv/nuccore/AF124929? Nov. 25, 2008 uploaded, [retrieved on Oct. 13, 2011] Mosher, R.H. et al., Definition: Streptomyces clavuligerus clavaminate synthase isozyme 1 (casI) gene, partial cds; putative deacetylcephalosporin C acetyltransferase (cvm4), putative luciferase (cvm5), and putative pyridoxal phosphate-dependent aminotransferase (cvm6) genes, complete cds; tRNA-Ala (trnA) gene, complete sequence; putative DNA binding protein (cvm9) gene, complete cds; and putative serine threonine protein kinase (cvm10) gene, partial cds., especially, gene 3114..4442.
Iwasaki et al., "Rittai Sentakuteki Amino-ki Ten'I Han'no ni yoru Kogaku Kassei Amino Kagobutsu no Gosei", Journal of the Agricultural Chemical Society of Japan, 2001, 75, special extra issue, p. 375, 3Y7p16.

* cited by examiner

*Primary Examiner* — Delia Ramirez
(74) *Attorney, Agent, or Firm* — Polsinelli PC

(57) ABSTRACT

A method for efficiently producing an optically active amino compound useful as an intermediate for pharmaceutical preparations, agricultural chemicals, or the like, from a ketone compound is provided. Specifically, a polypeptide having high resistance to a water-soluble organic solvent and novel transaminase activity for generating (S)-1-benzyl-3-pyrrolidinone with high optical purity of 93% or more, a gene encoding the same, and a transformant expressing the gene at a high level are also provided herein.

9 Claims, No Drawings

SEQUENCE LISTING

```
<160> NUMBER OF SEQ ID NOS: 7

<210> SEQ ID NO 1
<211> LENGTH: 445
<212> TYPE: PRT
<213> ORGANISM: Pseudomonas sp.

<400> SEQUENCE: 1

Met Asn His Leu Glu Lys Met Leu Glu Leu Asp Arg Asn His Leu Ile
1               5                   10                  15

His Pro His Leu Pro Lys Ser Glu Phe Ser Arg Thr Ile Phe Ala Arg
            20                  25                  30

Gly Lys Gly Cys Lys Leu Trp Asp Thr Glu Gly Arg Glu Tyr Leu Asp
        35                  40                  45

Ala Thr Gly Gly Leu Trp Leu Ala Gln Ile Gly His Gly Arg Glu Glu
    50                  55                  60

Ile Ala Glu Val Ala Ala Arg Gln Met Lys Gln Leu Glu Tyr Phe Thr
65                  70                  75                  80

Cys Phe Trp Asp Phe Ser Asn Glu Arg Ala Ile Glu Leu Ala Glu Lys
                85                  90                  95

Leu Ala Arg Leu Ala Pro Gly Asp Leu Glu Met Ser Phe Phe Thr Ser
            100                 105                 110

Gly Gly Ser Glu Gly Asp Asp Ala Ala Ile Lys Thr Ala Arg Tyr Tyr
        115                 120                 125

His Ser Gln Arg Gly Glu Pro Lys Arg Thr Trp Ile Leu Ser Arg Asn
    130                 135                 140
```

```
Asn Ala Tyr His Gly Leu Ala Tyr Gly Gly Thr Ala Thr Gly Phe
145                 150                 155                 160

Pro Glu Leu Arg Asp Gly Met Gly Pro Gly Leu Pro His Val Ala Tyr
                165                 170                 175

Leu Thr Gln Pro Asn Ala Tyr Arg His Tyr Tyr Phe Asp Gly Gln Asn
            180                 185                 190

Pro Thr Asp Phe Cys Val Ser Glu Leu Glu Lys Met Ile Ala Ser Ile
        195                 200                 205

Gly Ala Glu Asn Ile Ala Ala Met Ile Ala Glu Pro Ile Met Gly Val
    210                 215                 220

Gly Gly Met Val Pro Pro Val Asp Tyr Trp Pro Arg Met Ser Gln
225                 230                 235                 240

Val Leu Lys Lys Asn Gly Ile Leu Leu Ile Phe Asp Glu Val Val Ser
                245                 250                 255

Ala Phe Gly Arg Ser Gly His Trp Phe Ala Ala Glu Lys Tyr Gly Val
            260                 265                 270

Ile Pro Asp Ile Met Val Thr Ala Lys Gly Ile Ser Ser Gly Tyr Ile
        275                 280                 285

Pro Leu Gly Ala Val Ile Met Ser Arg Asp Val Ala Asp Thr Val Arg
    290                 295                 300

Glu Gly His Gly Tyr Pro Leu Gly Tyr Thr Tyr Ser Gly His Pro Val
305                 310                 315                 320

Ala Cys Ala Val Ala Leu Glu Asn Leu Arg Ile Leu Glu Asp Glu Asp
                325                 330                 335

Leu Ile Asn Arg Ser Asn His Met Gly Thr Tyr Ile Ala Glu Gln Leu
            340                 345                 350

Thr Ala Leu Arg Asp Asn Pro Cys Val Gly Glu Val Arg Gln Ala Gly
        355                 360                 365

Met Gly Ile Gly Ile Glu Leu Val Thr Asp Lys Glu Ser Arg Gln Pro
    370                 375                 380

Leu Pro Asp Ala Ala Leu Val Ile Pro Asp Ile Ile Arg Glu Glu Thr
385                 390                 395                 400

Gly Val Ile Val Arg Ile Ser Asn Ala Thr Asn Leu Cys Met Ser Pro
                405                 410                 415

Pro Leu Thr Met Ser Arg Glu Glu Ala Asp Arg Ala Val Glu Ala Val
            420                 425                 430

Cys Ser Val Leu Ser Arg Val Lys Pro Asp Gly Lys Val
        435                 440                 445

<210> SEQ ID NO 2
<211> LENGTH: 1335
<212> TYPE: DNA
<213> ORGANISM: Pseudomonas sp.

<400> SEQUENCE: 2
atgaatcacc ttgaaaaaat gcttgagttg gatcgcaatc acctgatcca ccctcaccta      60
ccgaagagcg agttcagccg cacgattttc gcacgcggca agggttgcaa actctgggac     120
acagaaggtc gcgaatacct ggatgcaact ggaggcctct ggctggcaca gattggccat     180
ggccgggagg aaatcgcgga ggtagcagct cgccagatga gcagctgga gtatttcacc      240 tgcttctggg acttctcaaa cgaacgcgca atcgagttgg cagagaagct agcccgtctt     300
gcacctggcg atctggaaat gagcttttc accagcggcg atcggagg cgatgacgca       360 gcaatcaaaa ctgctcgtta ctaccactct caacgcggcg aacccaagcg cacctggatc     420
```

```
ctgtcacgga caacgcccta ccacggcctg gcttacgggg gaggaacagc caccggcttt    480
ccggagctgc gcgacggtat gggccccggc ttaccccatg tcgcctatct aacccagccc    540
aatgcctacc ggcattatta cttcgacgga cagaacccca ctgacttctg tgtcagcgag    600
ctggagaaga tgatcgccag catcggcgcc gagaatatcg cagccatgat tgcggagcca    660
atcatggggg ttgggggaat ggttcccccg ccagtcgact actggcctcg catgtcacaa    720
gtgctcaaga aaaatggaat tctcctgata ttcgatgaag tggtgtcagc gtttggtcgc    780
tcaggtcatt ggttcgctgc cgagaagtac ggagtcatcc ctgacatcat ggtgaccgct    840
aagggtatct ccagcggcta cattcctctc ggtgcggtaa ttatgagccg agacgtagcc    900
gacaccgtcc gcgaaggcca tggctacccg ctcggttata catacagcgg ccatccagta    960
gcgtgcgcgg tagccttgga aaacctcagg atcctcgagg atgaagatct gatcaaccga   1020
tccaatcaca tgggtactta tatcgctgag caactcacgg cgctcaggga caacccttgc   1080
gtgggtgagg tgcgccaggc cgggatgggt atcggtattg aattggtcac ggataaagaa   1140
tcccgccaac cactcccgga tgcagcccta gtcatccccg acatcattcg cgaagaaact   1200
ggcgttatcg tgcgcatcag taacgcaaca aacctctgca tgtcgcctcc cctcacgatg   1260
agcagagagg aggccgatcg cgcggtcgag gctgtatgca gcgtactctc gcgggtaaag   1320
ccagacggca aagta                                                   1335

<210> SEQ ID NO 3
<211> LENGTH: 21
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n represents a, t, g or c.

<400> SEQUENCE: 3
atgaaycayy tngaraaarat g                                             21

<210> SEQ ID NO 4
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n represents a, t, g or c.
<220> FEATURE:
<221> NAME/KEY: misc_feature
<222> LOCATION: (18)..(18)
<223> OTHER INFORMATION: n represents a, t, g or c.

<400> SEQUENCE: 4
accatdatrt cnggdatnac                                                20

<210> SEQ ID NO 5
<211> LENGTH: 792
<212> TYPE: DNA
<213> ORGANISM: Pseudomonas sp.

<400> SEQUENCE: 5
cttgagttgg atcgcaatca cctgatccac cctcacctac cgaagagcga gttcagccgc     60
acgattttcg cacgcggcaa gggttgcaaa ctctgggaca cagaaggtcg cgaatacctg    120
```

```
gatgcaactg gaggcctctg gctggcacag attggccatg gccgggagga aatcgcggag    180
gtagcagctc gccagatgaa gcagctggag tatttcacct gcttctggga cttctcaaac    240
gaacgcgcaa tcgagttggc agagaagcta gcccgtcttg cacctggcga tctggaaatg    300
agcttttcca ccagcggcgg atcggagggc gatgacgcag caatcaaaac tgctcgttac    360
taccactctc aacgcggcga acccaagcgc acctggatcc tgtcacggaa caacgcctac    420
cacggcctgg cttacggggg aggaacagcc accggctttc cggagctgcg cgacggtatg    480
ggccccggct tacccatgt cgcctatcta acccagccca atgcctaccg gcattattac     540
ttcgacggac agaaccccac tgacttctgt gtcagcgagc tggagaagat gatcgccagc    600
atcggcgccg agaatatcgc agccatgatt gcggagccaa tcatgggggt tggggaatg     660 gttccccgc cagtcgacta ctggcctcgc atgtcacaag tgctcaagaa aaatggaatt     720
ctcctgatat tcgatgaagt ggtgtcagcg tttggtcgct caggtcattg gttcgctgcc    780
gagaagtacg ga                                                        792
```

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6

```
agcaagaggc aaccatatga atcaccttg                                       29
```

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7

```
taggctagtg agctcttata ctttgccgtc                                      30
```

NUCLEIC ACID ENCODING A POLYPEPTIDE HAVING AMINOTRANSFERASE ACTIVITY, VECTORS AND HOST CELLS COMPRISING THE NUCLEIC ACID

CROSS REFERENCE TO RELATED APPLICATIONS

This application is a National Phase filing under 35 U.S.C. § 371 of PCT/JP2011/072171 filed on Sep. 28, 2011; and this application claims priority to Application No. 2010-216547 filed in Japan on Sep. 28, 2010, under 35 U.S.C. § 119; the entire contents of all are hereby incorporated by reference.

TECHNICAL FIELD

The present invention relates to an enzyme capable of efficiently converting a ketone compound to an optically active amino compound through transamination and a method for producing an optically active amino compound using the enzyme. The thus obtained optically active amino compound can be used as an intermediate for pharmaceutical preparations, agricultural chemicals, or the like.

BACKGROUND ART

Regarding methods for producing optically active amino compounds using transaminases, there are many reports concerning methods for producing α-amino acid, but there are few reports concerning methods for producing optically active amino compounds other than α-amino acid. In recent years, a transaminase that generates optically active amino compounds other than α-amino acid has been discovered, and the use thereof for a general method for efficiently producing optically active amino compounds is expected.

However, transaminases known to date for generation of optically active amino compounds other than α-amino acid have had many problems (Non-patent Document 1).

For example, conventional transaminases are problematic in that they have low resistance to water-soluble organic solvents and the half-life of the enzyme activity decreases from about 5 hours to 3.5 hours or less when 10% v/v methanol, THF or DMF is added.

Among optically active amino compounds other than α-amino acid, a transaminase that generates (S)-1-benzyl-3-aminopyrrolidine, that is, a particularly useful pharmaceutical intermediate with high optical purity of 93% e.e. or more, has remained undiscovered (Patent Documents 1 and 2 and Non-patent Document 2).

PRIOR ART DOCUMENTS

Patent Documents

Patent Document 1: JP Patent Publication (Kokai) No. 2007-185133 A
Patent Document 2: WO2006/126498

Non-Patent Documents

Non-patent Document 1: Org. Biomol. Chem., 8, 1280-1283 (2010)
Non-patent Document 2: Adv. Synth. Catal. 350, 807-812 (2008)

SUMMARY OF THE INVENTION

Problems to be Solved by the Invention

An object of the present invention is to provide a method for efficiently producing optically active amino compounds useful as intermediates for pharmaceutical preparations, agricultural chemicals, and the like, from ketone compounds.

Means for Solving the Problem

As a result of screening for various soil isolates, the present inventors have discovered a microorganism having high resistance to a water-soluble organic solvent and generating (S)-1-benzyl-3-aminopyrrolidine with high optical purity of 93% e.e. or more. They have further succeeded in isolation and purification of a polypeptide having the activity from the microorganism. Moreover, as a result of thorough examination of the reaction properties of the polypeptide, they have discovered that the polypeptide exhibits high activity for a wide variety of ketone compounds, generates an optically active amino compound with high optical purity, and has high stability even in a water-soluble organic solvent. Furthermore, they have obtained a gene encoding the polypeptide by gene recombination techniques described later, and have revealed the nucleotide sequence thereof. Moreover, they have obtained using the gene a transformant capable of producing the polypeptide at a high level. Furthermore, they have established a method that involves examining the breeding conditions to allow industrial production of optically active amino compounds with high activity.

Specifically, the present invention relates to a polypeptide having the following physico-chemical properties (1) to (6).
(1) Function: It catalyzes transamination by acting on an amino group donor and 1-benzyl-3-pyrrolidinone to generate (S)-1-benzyl-3-aminopyrrolidine with optical purity of 93% e.e. or more.
(2) Substrate Specificity:
  (a) Amino group donor: It exhibits activity for (S)-1-phenethylamine, benzylamine, and ±2-butylamine and does not substantially exhibit activity for β-alanine and 4-aminobutyric acid.
  (b) Amino group receptor: It exhibits activity for pyruvic acid and activity for glyoxalic acid.
(3) Resistance to water-soluble organic solvent: It retains residual activity (after 2 hours of treatment with any one of 1-propanol, 2-propanol, and acetone having a final concentration of 80% v/v) equivalent to 10% or more of total activity before treatment.
(4) Optimum pH: 6.0 to 8.5
(5) Optimum temperature for action: 60° C.
(6) Thermal stability: It retains residual activity equivalent to 90% or more of total activity before treatment, when heated at 30° C. to 60° C. for 30 minutes.

The present invention further relates to a polypeptide consisting of an amino acid sequence that has 60% or more sequence identity with the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more.

The present invention further relates to a polypeptide consisting of an amino acid sequence that has a deletion, a substitution, an insertion, or an addition of 1 or more amino acids with respect to the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more.

The present invention further relates to DNA encoding the polypeptide, a vector containing the DNA, and a transformant resulting from transformation with the vector.

The present invention further relates to a method for producing an optically active amino compound, comprising causing the polypeptide or a culture product of the transformant to act on a ketone compound in the presence of an amino group donor.

The present invention further relates to a method for producing an optically active amino compound, comprising causing the polypeptide or a culture product of the transformant to act on an enantiomeric mixture of amino compounds in the presence of an amino group receptor.

This description includes part or all of the content as disclosed in the description and/or drawings of Japanese Patent Application No. 2010-216547, which is a priority document of the present application.

Effects of the Invention

Isolation of a polypeptide exhibiting high activity for a wide variety of ketone compounds, generating an optically active amino compound with high optical purity, and maintaining high activity even in a water-soluble organic solvent, and obtainment of a transformant with high capacity to produce the polypeptide make it possible to efficiently produce an optically active amino compound of interest.

EMBODIMENTS FOR CARRYING OUT THE INVENTION

The present invention is described in detail below. In addition, gene manipulation such as DNA isolation, vector construction, and transformation, which is described in detail in the Description, can be performed by methods described in a reference such as "Molecular Cloning 2nd Edition (Cold Spring Harbor Laboratory Press, 1989), Current Protocols in Molecular Biology (Greene Publishing Associates and Wiley-Interscience)" unless otherwise specified. Also, regarding the unit of enzyme activity, the amount of an enzyme that gives 1 μmol of a product per minute is designated as 1 U, unless otherwise specified.

1. Physico-Chemical Properties of the Polypeptide of the Present Invention

The polypeptide isolated by the following method in the present invention is a polypeptide having the following physico-chemical properties.

(1) Function: It catalyzes transamination by acting on 1-benzyl-3-pyrrolidinone in the presence of an amino group donor to generate (S)-1-benzyl-3-aminopyrrolidine with optical purity of 93% e.e. or more.

(2) Substrate Specificity:
(a) Amino group donor: It exhibits activity for (S)-1-phenethylamine, benzylamine, and ±2-butylamine and does not substantially exhibit activity for β-alanine and 4-aminobutyric acid.
(b) Amino group receptor: It exhibits activity for pyruvic acid and activity for glyoxalic acid.

(3) Resistance to water-soluble organic solvent: It retains residual activity (after 2 hours of treatment with any one of 1-propanol, 2-propanol, and acetone having a final concentration of 80% v/v) equivalent to 10% or more of total activity before treatment.

(4) Optimum pH: 6.0 to 8.5
(5) Optimum temperature for action: 60° C.
(6) Thermal stability: It retains residual activity equivalent to 90% or more of total activity before treatment, when heated at 30° C. to 60° C. for 30 minutes.

(Method for Determining Stereoselectivity for 1-benzyl-3-pyrrolidinone)

The polypeptide of the present invention catalyzes transamination by acting on 1-benzyl-3-pyrrolidinone in the presence of an amino group donor to generate (S)-1-benzyl-3-aminopyrrolidine with optical purity of 93% e.e. or more, preferably 95% e.e. or more, more preferably 97% e.e. or more, and most preferably 98% e.e. or more.

The above properties can be determined by the following method. Specifically, a purified polypeptide is added to a substrate solution having the following composition so that it has a final concentration ranging from 0.1 mg/mL to 1 mg/mL for reaction at 30° C. Furthermore, the reaction is continued until 0.6 mM or more 1-benzyl-3-aminopyrrolidine (as determined by the following quantitative analysis) is generated. After the completion of the reaction, the optical purity of the 1-benzyl-3-aminopyrrolidine generated in the reaction solution is analyzed by HPLC under the following conditions. When the optical purity of the thus generated (S)-1-benzyl-3-aminopyrrolidine varies depending on the amount of an enzyme used or the reaction time, the highest optical purity is employed.

[Composition of Substrate Solution]

| | |
|---|---|
| (S)-1-phenethylamine | 85.6 mM |
| 1-benzyl-3-pyrrolidinone | 57.1 mM |
| Pyridoxal phosphate | 0.5 mM |
| Potassium phosphate buffer (pH 7.0) | 0.1M |

[High Performance Liquid Chromatography Analysis Conditions]
<Quantitative Analysis>
Column: Finepak SIL C18-T (JASCO Corporation)
Eluent: distilled water 1260 mL/acetonitrile 740 mL/$KH_2PO_4$ 10 g/SDS 2.88 g (pH 3.6)
Flow rate: 1 mL/minute
Detection: 254 nm
Column temperature: 40° C.
<Analysis of Optical Purity>
A reaction solution is treated with an appropriate amount of sodium carbonate so that it became basic and then derivatized with dinitrobenzoyl chloride. If necessary, the resultant is purified by silica gel chromatography or the like and then analyzed under the following conditions.
Column: Chiralpak IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

(Substrate Specificity 1: Activity for Various Amines)
The polypeptide of the present invention exhibits activity for (S)-1-phenethylamine, benzylamine, and ±2-butylamine and does not substantially exhibit activity for β-alanine and 4-aminobutyric acid. Here, the expression "exhibits activity for (S)-1-phenethylamine" refers to that when transamination activity is determined by the following method, the amount of acetophenone generated per minute is 0.1 μmol or more, preferably 1 μmol or more, and more preferably 10 μmol or more with respect to 1 mg of a purified polypeptide.

The above transamination activity can be determined by the following method. Specifically, first, a purified polypeptide is added to a substrate solution having the following composition so that the total volume is 1 mL. After 5 minutes of reaction at 30° C., 0.05 mL of 6N hydrochloric acid is added to stop the reaction. The reaction solution is then analyzed by HPLC under the following conditions and then the quantity of the thus generated acetophenone is determined (hereinafter, referred to as "activity assay A").
Activity Assay A
[Composition of Substrate Solution]

| | |
|---|---|
| (S)-1-phenethylamine | 25 mM |
| Sodium pyruvate | 25 mM |
| Pyridoxal phosphate | 2.5 mM |
| Tris-hydrochloric acid buffer (pH 8.0) | 0.1M |

[High Performance Liquid Chromatography Analysis Conditions]
Column: Wakosil-II 5C18 RS (Wako Pure Chemical Industries, Ltd.)
Eluent: 10 mM potassium phosphate buffer (pH5.3): acetonitrile=3:2
Flow rate: 1 mL/minute
Detection: 241 nm Moreover, the expression "exhibits activity for benzylamine and ±2-butylamine" refers to a case in which when transamination activity is determined by the following method using the above amino compound as an amino group donor, the transamination activity is $1/10$ or more, preferably $1/5$ or more, and further preferably $1/2$ or more of that determined using (S)-1-phenethylamine. Furthermore, the expression "does not substantially exhibit activity for β-alanine and 4-aminobutyric acid" refers to a case in which when transamination activity is determined by the following method using the above amino compound as an amino group donor, the transamination activity is $1/50$ or less, preferably $1/100$ or less, and further preferably $1/1000$ or less of that determined using (S)-1-phenethylamine.

Transamination activity exhibited when the above amino group donor is used can be determined by the following method. Specifically, first, a purified polypeptide is added to a substrate solution with the following composition so that the volume thereof is 400 μl. After 1 hour of reaction at 30° C., 20 μl of 3N hydrochloric acid is added to stop the reaction. Next, 80 μl of a 0.2 M aqueous sodium carbonate solution and 200 μl of an acetone solution of 3.3 mg/mL Dabsyl chloride are separately added to 20 μl of the thus obtained reaction solution, followed by 10 minutes of reaction at 70° C. Acetic acid (20 μl) is added to the reaction solution and then the solution is stirred. The reaction solution is analyzed by HPLC under the following conditions, and then the quantity of dabsylated alanine is determined. In addition, the concentration of a purified polypeptide to be used herein is adjusted so that the amount of alanine generated is 2.8 mM or less as determined by the determination method (hereinafter, referred to as activity assay B).
Activity Assay B
[Composition of Substrate Solution]

| | |
|---|---|
| Various amino compounds | 14 mM |
| Pyruvic acid | 14 mM |
| Pyridoxal phosphate | 0.02 mM |
| Potassium phosphate buffer (pH 7.5) | 0.1M |

[High Performance Liquid Chromatography Analysis Conditions]
Column: Deverosil ODS-HG-3 (NOMURA CHEMICAL)
Eluent: acetonitrile/0.045 M acetate buffer (pH4.1)=35/65 (volume ratio)
Flow rate: 0.9 mL/minute
Detection: 254 nm
(Substrate Specificity 2: Activity for Glyoxalic Acid)

The polypeptide of the present invention exhibits activity for glyoxalic acid as an amino group receptor instead of pyruvic acid. Specifically, in the above activity assay A, transamination activity (determined when glyoxalic acid is used as an amino group receptor instead of pyruvic acid) equivalent to 10% or more, preferably 20% or more, and more preferably 30% or more is exhibited relative to activity determined using pyruvic acid as an amino group receptor and designated as 100%.
(Resistance to Water-Soluble Organic Solvent)

The polypeptide of the present invention exhibits high resistance to a water-soluble organic solvent. Specifically, it retains residual activity (after 2 hours of treatment with any one of 1-propanol, 2-propanol, and acetone having a final concentration of 80% v/v) equivalent to 10% or more of total activity before treatment.

The concentration of a water-soluble organic solvent to be used herein is 10% v/v, preferably 30% v/v, more preferably 50% v/v, and most preferably 80% v/v. The polypeptide retains residual activity after treatment with a water-soluble solvent, which is equivalent to 10% or more, preferably 20% or more, more preferably 30% or more, further preferably 50%, and most preferably 80% or more.

Here, the term "water-soluble organic solvent" refers to a solvent that is mixed in an arbitrary ratio with water. Examples thereof include acetic acid, acetone, acetonitrile, DMF, DMSO, ethanol, methanol, 2-propanol, 1-propanol, and THF. Preferable examples thereof include 1-propanol, 2-propanol, and acetone.

With high resistance to a water-soluble organic solvent, improvement in reactivity also to a substrate with low water solubility can be expected, for example.

Resistance to a water-soluble organic solvent can be determined by the following method. Specifically, first, 800 uL of each water-soluble organic solvent is added to 200 uL of a 0.1 M aqueous potassium phosphate solution (pH7.5) supplemented with 0.5 mM PLP containing a purified polypeptide, so that the solvent is brought into contact with the solution at 30° C. for 2 hours. Subsequently, the resultant is diluted with a 0.1 M aqueous potassium phosphate solution supplemented with 0.5 mM PLP. Activity in the dilute solution is compared with the same in a purified polypeptide solution before addition of the solvent using the above activity assay A.
(Optimum pH)

The optimum pH for transamination is determined by the above activity assay A using combinations of the following buffers and pHs. The term "optimum pH" refers to pH at which activity of 80 or more is exhibited when the highest activity level is designated as "100" in this assay. When activity levels are different depending on buffer types, the activity level higher than the other is employed even if the pHs are the same.
pH4.0, 4.5, 5.0, 5.5: 0.1 M sodium acetate buffer
pH6.0, 6.5, 7.0, 7.5, 8.0: 0.1 M potassium phosphate buffer
pH7.5, 8.0, 8.5, 9.0: 0.1M Tris-hydrochloric acid buffer
(Optimum Temperature)

The optimum temperature for transamination is a temperature at which the highest activity level is exhibited upon determination using the above "activity assay A" from among the reaction temperatures of 10° C., 20° C., 30° C., 40° C., 50° C., 60° C., and 70° C.

(Thermal Stability)

The thermal stability of the polypeptide is determined as follows. In 0.1 M potassium phosphate buffer (pH 7.5) containing 0.5 mM pyridoxal phosphate, the purified polypeptide is heated at 30° C., 40° C., 50° C., 60° C., 70° C., or 80° C. for 30 minutes, and then activity is determined as described in the above "activity assay A." The polypeptide can be said to have thermal stability if it exhibits, after heat treatment, residual activity equivalent to 90% or more of the activity before heat treatment (designated as 100%).

(Molecular Weight)

The polypeptide of the present invention has a molecular weight of about 50,000, which can be determined by 10% SDS-polyacrylamide gel electrophoresis based on mobility relative to that of a standard protein.

2. Isolation of the Polypeptide of the Present Invention

Examples of the polypeptide of the present invention include any polypeptide, as long as it exhibits the above properties. For example, the polypeptide can be obtained from a microorganism belonging to the genus *Pseudomonas*. Examples of such a microorganism that serves as an origin of the polypeptide of an embodiment of the present invention include preferably *Pseudomonas* sp. that can be easily obtained by persons skilled in the art from public coordinated collections of microorganisms (e.g., NBRC), and further preferably, *Pseudomonas* sp. MV37. The *Pseudomonas* sp. MV37 was deposited under accession No. NITE P-953 on Jun. 11, 2010 with the NITE Biological Resource Center (NBRC) (NITE: the National Institute of Technology and Evaluation) (2-5-8 Kazusa Kamatari, Kisarazu, Chiba, Japan, 292-0818).

(Medium Components)

As a culture medium for a microorganism having the polypeptide of the present invention, a general liquid nutritional medium containing a carbon source, a nitrogen source, an inorganic salt, an organic nutrient, and the like can be used, as long as the microorganism grows therein.

In addition, when the microorganism is cultured, as an inducer for the polypeptide of the present invention, an amino compound such as propylamine, 1-butyl amine, 2-butyl amine, 2-pentylamine, isopropylamine, isobutyl amine, 7-methoxy-2-aminotetralin, 1-phenethylamine, and 1-benzyl-3-aminopyrrolidine can be added to a medium, and then the microorganism can be cultured. The inducer may be used independently or 2 or more types of inducer may be mixed and then used. The amount of the inducer to be added herein is not particularly limited, but is preferably in view of inhibition of microbial growth, generally 1% by weight or less in a general medium composition. The time for adding the above inducer is not particularly limited and the inducer may be added at the start of culture or during culture. Furthermore, to enhance the effect of the inducer, a fewer amount of a general carbon source, nitrogen source, inorganic salt, or organic nutrient other than the inducer can be effective in some cases.

(Purification of Polypeptide)

The polypeptide of the present invention can be purified from a microorganism that produces the polypeptide by a protein purification method known by persons skilled in the art. For example, cells are collected by centrifugation or filtration from culture solutions of the microorganism, the thus obtained cells are disrupted by a physical technique using an ultrasonic disintegrator, glass beads, or the like, cell residues are removed by centrifugation to prepare a cell-free extract, the cell-free extract is subjected to fractional precipitation, ion exchange chromatography, hydrophobic chromatography, gel filtration chromatography, reverse phase chromatography, ultrafiltration, or the like, and thus the polypeptide of interest can be isolated.

3. The Amino Acid Sequence of the Polypeptide of the Present Invention

Examples of the polypeptide of the present invention include the following polypeptides (a) to (c):
(a) a polypeptide consisting of the amino acid sequence shown in SEQ ID NO: 1 in the sequence listing;
(b) a polypeptide consisting of an amino acid sequence that has a deletion, a substitution, an insertion, and/or an addition of 1 or more amino acids with respect to the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more;
(c) a polypeptide consisting of an amino acid sequence that has 60% or more sequence identity with the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more.

A polypeptide consisting of an amino acid sequence that has a substitution, an insertion, a deletion and/or an addition of 1 or more amino acids with respect to the amino acid sequence shown in SEQ ID NO: 1 in the sequence listing can be prepared according to a known method described in "Current Protocols in Molecular Biology (John Wiley and Sons, Inc., 1989)" or the like. The thus prepared polypeptide is included in the above polypeptide as long as it has activity to act on 1-benzyl-3-pyrrolidinone in the presence of an amino group donor to generate (S)-1-benzyl-3-aminopyrrolidine having optical purity of 93% e.e. or more.

In the amino acid sequence shown in SEQ ID NO: 1 in the sequence listing, site(s) to be subjected to substitution, insertion, deletion and/or addition of an amino acid(s) are not particularly limited, but a highly conserved region is preferably avoided. Here, the term "highly conserved region" refers to a position at which amino acids match among a plurality of sequences when the amino acid sequences of a plurality of enzymes (polypeptides) from different origins are optimally aligned and compared. Such a highly conserved region can be confirmed by comparing the amino acid sequence shown in SEQ ID NO: 1 with the amino acid sequence of transaminase (polypeptide) derived from another microorganism described above, using a tool such as GENETYX.

An amino acid sequence modified by substitution, insertion, deletion, and/or addition may contain only 1 type of modification (e.g., substitution), or 2 or more types of modification (e.g., substitution and insertion). In the case of substitution, an amino acid(s) to be substituted is preferably an amino acid (homologous amino acid) having properties analogous to those of an amino acid before substitution. Here, amino acids within the same group are regarded as homologous amino acids.
(Group 1: Neutral non-polar amino acid) Gly, Ala, Val, Leu, Ile, Met, Cys, Pro, Phe
(Group 2: Neutral polar amino acid) Ser, Thr, Gln, Asn, Trp, Tyr
(Group 3: Acidic amino acid) Glu, Asp
(Group 4: Basic amino acid) His, Lys, Arg.

The term "(one or) more amino acids" above refers to 60, preferably 20, more preferably 15, further preferably 10, and further preferably 5, 4, 3, or 2 or less amino acids, for example.

Sequence identity with the amino acid sequence shown in SEQ ID NO: 1 in the sequence listing is preferably 60% or more, more preferably 70% or more, further preferably 80% or more, further more preferably 85% or more, still further more preferably 90% or more, and most preferably 95% or more.

The sequence identity of an amino acid sequence is represented by a value obtained by comparing the amino acid sequence shown in SEQ ID NO: 1 in the sequence listing with an amino acid sequence to be evaluated, dividing the number of positions at which amino acids of the two sequences match by the total number of amino acids compared, and then multiplying the result by 100.

An additional amino acid sequence can be bound to the amino acid sequence shown in SEQ ID NO: 1 as long as the polypeptide has activity to act on 1-benzyl-3-pyrrolidinone in the presence of an amino group donor to generate (S)-1-benzyl-3-aminopyrrolidine with optical purity of 93% e.e. or more. For example, a tag sequence such as a histidine tag or an HA tag can be added. Alternatively, the polypeptide of the present invention can be fused to another protein to prepare a fusion protein. Also, the polypeptide of the present invention may be a peptide fragment as long as it has the above transamination activity.

4. Cloning of DNA Encoding the Polypeptide of the Present Invention

The DNA of the present invention encodes the above polypeptide. The DNA may be any DNA that can express the polypeptide within host cells into which it is introduced according to a method described later, and may contain an arbitrary untranslated region. Persons skilled in the art can easily obtain the DNA of the present invention based on SEQ ID NO: 2 in the sequence listing through chemical synthesis. Regarding another method, persons skilled in the art can obtain the DNA from a microorganism serving as an origin of the polypeptide by a known method, as long as the purified polypeptide can be obtained.

As a method for obtaining the DNA of the present invention, an example using the above *Pseudomonas* sp. MV37 is described below, but the method employed in the present invention is not limited thereto.

First, the above polypeptide purified from a cell-free extract of the microorganism is digested with appropriate endopeptidase, fragments cleaved by reverse phase HPLC are purified, and then a portion of or the entire amino acid sequence is determined using a type ABI492 protein sequencer (Applied Biosystems), for example. Based on the thus obtained amino acid sequence information, PCR (Polymerase Chain Reaction) primers for amplification of a portion of DNA encoding the polypeptide are synthesized. Next, the chromosomal DNA of a microorganism serving as an origin of the polypeptide is prepared by a general DNA isolation method such as a method of Visser et al. (Appl. Microbiol. Biotechnol., 53, 415 (2000)). PCR is performed using the chromosomal DNA as a template and the above-mentioned PCR primers, a portion of DNA encoding the polypeptide is amplified, and thus the nucleotide sequence thereof is determined. The nucleotide sequence can be determined using a type ABI373A DNA Sequencer (Applied Biosystems), for example. If the nucleotide sequence of a portion of DNA encoding the polypeptide is revealed, for example, the entire sequence can be determined by an inverse PCR method (Nucl. Acids Res., 16, 8186 (1988)).

An example of the thus obtained DNA of the polypeptide is DNA containing the nucleotide sequence shown in SEQ ID NO: 2 in the sequence listing.

The nucleotide sequence shown in SEQ ID NO: 2 in the sequence listing is as described below.

5. The Nucleotide Sequence of DNA Encoding the Polypeptide of the Present Invention Examples of DNA encoding the polypeptide of the present invention include the following DNAs (A) to (C):

(A) DNA consisting of the nucleotide sequence shown in SEQ ID NO: 2 in the sequence listing;
(B) DNA hybridizing under stringent conditions to DNA consisting of a nucleotide sequence complementary to the nucleotide sequence shown in SEQ ID NO: 2 in the sequence listing;
(C) DNA consisting of a nucleotide sequence that has a substitution, a deletion, an insertion, and/or an addition of 1 or more nucleotides with respect to the nucleotide sequence shown in SEQ ID NO: 2 in the sequence listing.

Here, the expression "DNA hybridizing under stringent conditions to DNA consisting of a nucleotide sequence complementary to the nucleotide sequence shown in SEQ ID NO: 2 in the sequence listing" refers to DNA that is obtained by a colony•hybridization method, a plaque•hybridization method, a Southern hybridization method, or the like under stringent conditions using DNA as a probe consisting of a nucleotide sequence complementary to the nucleotide sequence shown in SEQ ID NO: 2 in the sequence listing.

Hybridization can be performed according to the method described in "Molecular Cloning, A laboratory manual, second edition (Cold Spring Harbor Laboratory Press, 1989)" or the like. Here, the term "DNA hybridizing under stringent conditions" refers to DNA that can be obtained by performing hybridization at 65° C. in the presence of 0.7 to 1.0 M NaCl using a filter to which colony- or plaque-derived DNA has been immobilized, and then washing the filter at 65° C. using a 2×SSC solution (the composition of a 1×SSC solution: 150 mM sodium chloride and 15 mM sodium citrate). Furthermore the term refers to DNA that can be obtained by washing preferably with a 1×SSC solution at 65° C., more preferably with a 0.5×SSC solution at 65° C., further preferably with a 0.2×SSC solution at 65° C., and most preferably with a 0.1×SSC solution at 65° C.

Hybridization conditions are as described above, but are not particularly limited to these conditions. Elements affecting hybridization stringency may be a plurality of elements such as temperature and salt concentration. Persons skilled in the art can realize the optimum stringency by adequately selecting these elements.

An example of DNA capable of hybridizing under the above conditions is DNA having 70% or more, preferably 74% or more, more preferably 79% or more, further more preferably 85% or more, and most preferably 90% or more sequence identity with the DNA shown in SEQ ID NO: 2. As long as the polypeptide encoded by such DNA has the above transamination activity, it is included in examples of the above DNA.

The sequence identity (%) of DNA is represented by a numerical value obtained by optimally aligning two DNAs to be compared, dividing the number of positions at which nucleobases match (e.g., A, T, C, G, U, or I) between the two sequences by the total number of nucleotides compared, and then multiplying the result by 100.

DNA sequence identity can be calculated using the following sequencing tool, for example: GCG Wisconsin Package (Program Manual for The Wisconsin Package, Version 8, September 1994, Genetics Computer Group, 575 Science Drive Medison, Wis., U.S.A. 53711; Rice, P. (1996) Program Manual for EGCG Package, Peter Rice, The Sanger Centre, Hinxton Hall, Cambridge, CB10 1RQ, England), and, the ExPASy World Wide Web Molecular Biology Server (Geneva University Hospital and University of Geneva, Geneva, Switzerland).

Here, the term "DNA that has a substitution, a deletion, an insertion, and/or an addition of 1 or more nucleotides with respect to the nucleotide sequence shown in SEQ ID NO: 2 in the sequence listing" can be prepared according to a known method described in "Current Protocols in Molecular Biology (John Wiley and Sons, Inc., 1989)," for example.

A site(s) of the nucleotide sequence shown in SEQ ID NO: 2 in the sequence listing, which is subjected to substitution, insertion, deletion, and/or addition of a nucleotide(s) is not particularly limited. Preferably a highly conserved region is avoided to prevent frame shift from taking place. Here, the term "highly conserved region" refers to a position(s) at which nucleotides match among a plurality of sequences when the nucleotide sequences of a plurality of enzymes from different origins are optimally aligned and compared. Such a highly conserved region can be confirmed by comparing the nucleotide sequence shown in SEQ ID NO: 2 with the nucleotide sequence of a transaminase gene derived from a known microorganism using a tool such as GENETYX.

A nucleotide sequence modified by substitution, insertion, deletion, and/or addition may contain only 1 type of modification (e.g., substitution) or 2 or more types of modification (e.g., substitution and insertion).

The above term "(one or) more nucleotides" refers to 150, preferably 100, more preferably 50, further preferably 20, 10, 5, 4, 3, or 2 or less nucleotides, for example.

6. Vector

Vector DNA to be used for introducing the DNA of an embodiment of the present invention into a host microorganism and then causing the expression of the DNA in the host microorganism may be any vector that enables expression of the gene encoded by the DNA within an appropriate host microorganism. Examples of such vector DNA include a plasmid vector, a phage vector, and a cosmid vector. Furthermore, a shuttle vector that enables gene exchange with another host strain can be used herein.

Such a vector contains a regulatory factor of an operably linked promoter (e.g., lacUV5 promoter, trp promoter, trc promoter, tac promoter, lpp promoter, tufB promoter, recA promoter, and pL promoter) can be preferably used as a vector containing an expression unit operably linked to the DNA of the present invention. Examples thereof include pUC18 (Toyobo Co., Ltd.), pUC19 (Toyobo Co., Ltd.), and pUCNT (International Publication WO94/03613).

The term "regulatory factor" refers to a nucleotide sequence having a functional promoter and an arbitrary related transcriptional element (e.g., enhancer, CCAAT box, TATA box, and SPI site).

Furthermore, the term "operably linked" refers to that various regulatory elements regulating gene expression such as a promoter and an enhancer are ligated to a gene so that they can function within the host cells. Types and kinds of regulatory factor can be varied depending on host, which is a matter known by persons skilled in the art.

Vectors, promoters, and the like that can be used in various organisms are specifically described in "Basic Microbiology (Biseibutsu-gaku Kiso-ko-za) 8 genetic engineering (KYORITSU SHUPPAN CO., LTD, 1987)," for example.

7. Host and Transformant

Host organisms to be used for expressing the DNA of an embodiment of the present invention are not particularly limited, as long as they are organisms that are transformed with an expression vector containing DNA encoding each polypeptide and can express the polypeptide in which the DNA has been introduced. Examples of microorganisms that can be used herein include bacteria for which host vector systems have been developed, such as bacteria of the genus *Escherichia*, the genus *Bacillus*, the genus *Pseudomonas*, the genus *Serratia*, the genus *Brevibacterium*, the genus *Corynebacterium*, the genus *Streptococcus*, or the genus *Lactobacillus*, actinomycetes for which host vector systems have been developed, such as those of the genus *Rhodococcus* or the genus *Streptomyces*, yeast for which host vector systems have been developed such as that of the genus *iSaccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, or the genus *Candida*, and molds for which host vector systems have been developed such as those of the genus *Neurospora*, the genus *Aspergillus*, the genus *Cephalosporium*, or the genus *Trichoderma*. Furthermore, various host•vector systems have been developed for plants and animals other than microorganisms. Systems for expressing heteroproteins in large amounts in particularly insects (such as silkworm) (Nature 315, 592-594 (1985)) or plants such as rapeseed, corn, or potato have been developed and can be appropriately used. Of these, bacteria are preferred in terms of introduction and expression efficiency and *Escherichia coli* is particularly preferred.

An expression vector containing the DNA of the present invention can be introduced into a host microorganism by a known method. For example, when *Escherichia coli* is used as a host microorganism, the vector can be introduced into host cells using commercially available *E. coli* HB101 competent cells (Takara Bio Inc.).

8. Method for Producing an Optically Active Amino Compound

Next, a method for producing an optically active amino compound using the polypeptide of an embodiment of the present invention or a microorganism capable of producing the polypeptide is as described below.

Examples of a microorganism capable of producing the polypeptide of an embodiment of the present invention include the above *Pseudomonas* sp. MV37 and a transformant in which a vector containing the DNA of an embodiment has been introduced.

Examples of the method for producing an optically active amino compound of the present invention include a method (hereinafter, referred to as "production method I") that involves transferring an amino group from an amino group donor to a ketone compound having the same backbone as that of an amino compound of interest, and collecting the thus generated optically active amino compound and a method (hereinafter, referred to as "production method II") that involves selectively transferring, from an enantiomeric mixture of amino compounds, an amino group (of either one of enantiomers) to an amino group receptor and then collecting the remaining enantiomer (optically active amino compound).

First, the production method I is as described below.

(Production Method I)

The production method I comprises causing the polypeptide of the present invention or the culture product of a transformant capable of producing the polypeptide to act on a ketone compound in the presence of an amino group donor, so as to produce an optically active amino compound.

The production method comprises causing

[Chemical formula 1]

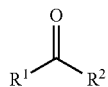

(1)

the polypeptide of the present invention or the culture product of a microorganism capable of producing the polypeptide to act on a ketone compound represented by general formula (1) in the presence of an amino group donor,

[Chemical formula 2]

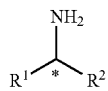

(2)

to produce an optically active amino compound represented by general formula (2), for example.

In formulae (1) and (2) above, $R^1$ and $R^2$ denote alkyl groups that may be substituted, aralkyl groups that may be substituted or aryl groups that may be substituted, and $R^1$ and $R^2$ may bind to each other to form a ring. However, $R^1$ and $R^2$ are structurally different.

$R^1$ and $R^2$ are preferably C1-20 alkyl groups that may be substituted, aralkyl groups that may be substituted, or aryl groups that may be substituted, and are more preferably C1-10 alkyl groups that may be substituted, aralkyl groups that may be substituted, or aryl groups that may be substituted.

Examples of an aryl group include a phenyl group, a naphthyl group, a pyridyl group, a thienyl group, an oxadiazolyl group, an imidazolyl group, a thiazolyl group, a furyl group, a pyrrolyl group, a phenoxy group, a naphthoxy group, a pyridyloxy group, a thienyloxy group, an oxadiazolyloxy group, an imidazolyloxy group, a thiazolyloxy group, a furyloxy group, and a pyrrolyloxy group.

Examples of an alkyl group include a methyl group, an ethyl group, a propyl group, a butyl group, a pentyl group, a hexyl group, an isopropyl group, a sec-butyl group, a tert-butyl group, a methoxy group, an ethoxy group, a tert-butoxy group, a methoxycarbonyl group, an ethoxycarbonyl group, a tert-butoxycarbonyl group, a vinyl group, an allyl group, a cyclopentyl group, a cyclohexyl group, and a cycloheptyl group. Examples of an aralkyl group include a benzyl group and the like.

These groups may be further substituted. Examples of a substituent include a halogen atom, a nitrogen atom, a sulfur atom, a hydroxy group, a nitro group, a cyano group, a methoxy group, an ethoxy group, a carboxyl group, a carboxymethyl group, a carboxyethyl group, and methylenedioxy. Furthermore, a ring may be formed via a substituent.

Specific examples of the above ketone compound include 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, and 3,4-dimethoxyphenyl acetone.

(Amino Group Donor)

As an amino group donor, any amino group donor can be used as long as it is an amino compound on which the polypeptide of the present invention acts. Specific examples thereof include 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, 3-amino-1-phenylbutane, benzylamine, β-phenethylamine, cyclohexylamine, and optically active compounds thereof. Of these, 1-phenethylamine and alanine are preferred.

(Form of Polypeptide)

In the production method I, the polypeptide of the present invention or the culture product of a microorganism capable of producing the polypeptide is caused to act on the ketone compound in the presence of an amino group donor.

Here, the term "culture product" refers to a culture solution containing cells, cultured cells, or a processed product thereof. Here, the term "processed product thereof" refers to, for example, a cell-free extract, lyophilized cells, acetone-dried cells, or a pulverized product of cells. Moreover, the polypeptides and culture products thereof can be used in the form of immobilized enzymes or immobilized cells. Immobilization can be performed by a method known by persons skilled in the art (e.g., a crosslinking method, a physical adsorption method, or an integrated immobilization method).

(Improvement of Reactivity by Solving the Reaction Equilibrium Problem and the Product Inhibition)

Amination using transamination is generally a reversible reaction, so that in general it apparently stops at an equilibrium point. A reaction using the polypeptide of the present invention can be improved by combining known methods for solving such reaction equilibrium problem. For example, an effective method for solving the reaction equilibrium problem involves using alanine as an amino group donor, conjugating lactate dehydrogenase and glucose dehydrogenase for coenzyme regeneration, and converting pyruvic acid to be produced as a by-product to lactic acid, as described in WO2007/139055A. Similarly, examples of an effective method include a method that involves using alanine as an amino group donor and removing pyruvic acid to be produced as a by-product with pyruvate decarboxylase (WO2007/093372A1), a method using alanine dehydrogenase (US2009/0117627A1, Evonik Degussa GmbH), a method using hydrogen peroxide for removal (US2008/0213845A1), and a method using acetobutyrate synthase (Biosci. Biotechnol. Biochem. 72(11), 3030-3033 (2008)).

(Substrate Concentration)

Regarding the concentration of a substrate to be used for reaction, the concentration of a ketone compound ranges from 0.1% by weight to 80% by weight and preferably ranges from 1% by weight to 50% by weight in the composition of a reaction solution. Moreover, in the case of chiral amine, an amino group donor is preferably used so that the concentration ranges from 80 mol % to 1200 mol %, and preferably 100 mol % to 600 mol % with respect to that of a ketone compound. In addition, when a racemic amino compound is used as the above amino group donor, it can be used so that the concentration of one of the racemic compounds is as described above.

(Reaction pH)

Regarding the optimum pH for the polypeptide of the present invention to act, the lower limit thereof is preferably pH 5.0 or more, and more preferably pH 6.0 or more, and the upper limit thereof is preferably pH 10.0 or less and more preferably pH 9.0 or less.

When a plurality of polypeptides are conjugated, pH at which all polypeptides to be used herein can stably and highly actively act is preferably selected.
(Reaction Temperature)

Regarding the reaction temperature for the polypeptide of the present invention, it is preferably 25° C. or higher, more preferably 30° C. or higher, preferably 60° C. or lower, and more preferably 50° C. or lower in view of optimum temperature and thermal stability.

When a plurality of polypeptides are conjugated, the reaction temperature at which all polypeptides to be used herein stably and highly actively act is preferably selected.
(Solvent)

As a reaction solvent, an aqueous medium such as ion exchanged water or buffer is generally used. Reaction can also be performed with a system containing an organic solvent. As an organic solvent, for example, an alcohol-based solvent such as methanol, ethanol, 1-propanol, 2-propanol, and 1-butanol, an aliphatic hydrocarbon-based solvent such as pentane and hexane, an aromatic hydrocarbon-based solvent such as benzene and toluene, a halogenated hydrocarbon-based solvent such as methylene chloride and chloroform, an ether-based solvent such as diethyl ether and diisopropylether, an ester-based solvent such as ethyl acetate and butyl acetate, a ketone-based solvent such as acetone and methyl ethyl ketone, or another solvent such as acetonitrile can be adequately used.
(2-Phase System)

If necessary, the above organic solvent is added to water to a level exceeding its solubility to water and then reaction can be performed with the 2-phase system. An organic solvent is also caused to coexist in such a reaction system, so that selectivity, conversion rate, yield, and the like are improved in many cases.
(Reaction Time)

The time for reaction generally ranges from 1 hour to 1 week and preferably ranges from 1 to 72 hours. Reaction conditions under which reaction is completed within such reaction duration are preferably selected.
(Extraction and Purification)

An optically active amino compound is generated by the above reaction. The thus generated optically active amino compound can be isolated from a reaction mixture by a known method such as extraction, distillation, recrystallization, and column separation.

For example, after adjustment of pH to acidic, an unreacted substrate and a ketone compound (resulting from transamination) corresponding to an amino group donor can be selectively removed with the use of a general solvent (e.g., ethers such as diethyl ether and diisopropylether, esters such as ethyl acetate and butyl acetate, hydrocarbons such as hexane, octane, and benzene, and halogenated hydrocarbons such as methylene chloride), while leaving an optically active amino compound generated in an aqueous phase.

The thus generated optically active amino compound and unreacted amino group donor can be extracted similarly with a general organic solvent after adjustment of the pH to basic, for example. The thus generated optically active amino compound and unreacted amino group donor can be separated by distillation, for example.
(Production Method II)

Next, the production method II of the present invention is as described below.

The production method is a method for producing an optically active amino compound, comprising causing the polypeptide of the present invention or the culture product of a transformant capable of producing the polypeptide to act on an enantiomeric mixture of amino compounds in the presence of an amino group receptor.

According to the production method, for example,

[Chemical formula 3]

(3)

the polypeptide of the present invention or the culture product of a microorganism capable of producing the polypeptide is caused to act on an enantiomeric mixture of amino compounds represented by general formula (3) in the presence of an amino group receptor,

[Chemical formula 4]

(2)

so that an optically active amino compound represented by general formula (4) can be obtained.

$R^1$ and $R^2$ in the above formulae (3) and (4) are the same as $R^1$ and $R^2$ in the above formulae (1) and (2).

Specific examples of the above optically active amino compound include 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, and 3,4-dimethoxyamphetamine.
(Amino Group Receptor)

In the method, a ketone compound is used as an amino group receptor. The ketone compound may be any ketone compound as long as it has activity as an amino group receptor, and is preferably, pyruvic acid or glyoxalic acid.

In the production method II, the polypeptide of the present invention or the culture product of a transformant capable of producing the polypeptide is caused to act on an enantiomeric mixture of amino compounds in the presence of the amino group receptor.

Here, the term "an enantiomeric mixture of amino compounds" refers to a mixture of an enantiomer and its corresponding (mirror-image) enantiomer. In general, a racemic body is inexpensive and can be easily obtained, and thus such a racemic body is preferably used herein. However, examples of an enantiomeric mixture are not limited to racemic bodies. For example, with the use of a mixture containing an enantiomer in an amount slightly higher than that of its mirror-image enantiomer, the optical purity thereof can be preferably increased by the production method II.

In addition, what is meant by the culture product is similar to that in the case of the above production method I.

Furthermore, the concentration of an amino compound ranges from 0.1% by weight to 80% by weight and preferably ranges from 1% by weight to 50% by weight in the composition of a reaction solution. The concentration of an amino group receptor to be preferably employed herein ranges from 30 mol % to 100 mol %, and preferably ranges from 50 mol % to 60 mol % with respect to that of an amino compound. Regarding reaction pH, reaction temperature, and reaction solvent, conditions similar to those for the production method I can be employed.

An optically active amino compound is generated by the above reaction. The thus generated optically active amino compound can be isolated from a reaction mixture by a method similar to the production method I.

EXAMPLES

The present invention is hereafter described in greater detail with reference to the following examples, although the present invention is not limited thereto.

Example 1

Obtainment and Analysis of Soil Isolates

An MV37 strain, an MV38 strain, an MV45 strain, and an MV48 strain isolated from soil were each cultured with aeration using N medium (composition: 50 g/L polypeptone (Nihon Pharmaceutical Co., Ltd.), 30 g/L D-glucose, 20 g/L NaCl, 2 g/L yeast extract (Difco), g/L (RS)-1-phenethylamine (pH 7.0)) at 28° C. for 62 hours. Subsequently, 2 mL of each culture solution was centrifuged, the following substrate solution (400 uL) was added to the thus obtained cells, and then the resultant was stirred at 30° C. for 2 hours for reaction. The thus generated 1-benzyl-3-aminopyrrolidine was subjected to quantitative analysis and analysis of optical purity under the following conditions.

As a result, the results for the MV37 strain were a conversion rate of 2.0% and optical purity of 98.0% e.e. (S-configuration), the results for the MV38 strain were a conversion rate of 1.3% and optical purity of 97.4% e.e. (S-configuration), the results for the MV45 strain were a conversion rate of 1.8% and optical purity of 97.9% e.e. (S-configuration), and the results for the MV48 strain were a conversion rate of 2.5% and optical purity of 97.6% e.e. (S-configuration).

Furthermore, the MV38 strain, the MV45 strain, and the MV48 strain were analyzed for a 16SrDNA partial sequence (about 500 bp). As a result, all strains were assumed to belong to the genus *Pseudomonas*. The MV37 strain was analyzed for 16SrDNA (1492 bp), so that it was assumed to belong to *Pseudomonas* sp. closely related to *Pseudomonas monteilii*, *Pseudomonas fluva*, *Pseudomonas oryzihabitans*, and *Pseudomonas putida*.

[Composition of Substrate Solution]

| | |
|---|---|
| L-alanine | 100 mM |
| 1-benzyl-3-pyrrolidinone | 7.5 mM |
| Pyridoxal phosphate | 0.5 mM |
| Potassium phosphate buffer (pH 7.0) | 0.05M |

[High Performance Liquid Chromatography (HPLC) Quantitative Analysis Conditions]
<Quantitative Analysis>
Column: Finepak SIL C18-T (JASCO Corporation)
Eluent: distilled water 1260 mL/acetonitrile 740 mL/$KH_2PO_4$ 10 g/SDS 2.88 g (pH 3.6)
Flow rate: 1 mL/minute
Detection: 254 nm
Column temperature: 40° C.

[Conditions for Optical Purity Analysis by High Performance Liquid Chromatography (HPLC)]
A reaction solution was treated with an appropriate amount of sodium carbonate so that it became basic, derivatized with dinitrobenzoyl chloride, and then analyzed under the following conditions.
Column: Chiralpak IA (Daicel Corporation)
Eluent: hexane/ethanol/diethylamine/acetonitrile=800/200/1/5 (volume ratio)
Flow rate: 0.8 mL/minute
Detection: 254 nm Example 2

Purified TPM Preparation 1

*Pseudomonas* sp. MV37 (NITE P-953) analyzed in Example 1 was cultured using 5 mL of Npre medium (composition: 50 g/L polypeptone (Nihon Pharmaceutical Co., Ltd.), 30 g/L D-glucose, 20 g/L NaCl, 2 g/L yeast extract (Difco) (pH 7.0)) at 30° C. for 1 day, so that a first starter culture solution was obtained.

Next, in a 500-mL Sakaguchi flask, 500 µL of the first starter culture solution was inoculated into 60 mL of N medium (composition: 50 g/L polypeptone (Nihon Pharmaceutical Co., Ltd.), 30 g/L D-glucose, 20 g/L NaCl, 2 g/L yeast extract (Difco), 1 g/L (RS)-1-phenethylamine (pH7.0)) followed by 7 hours of culture at 28° C. Thus, a second starter culture solution was obtained.

Next, 30 mL of the second starter culture solution was inoculated into 3.0 L of N medium in a 5-liter mini jar, followed by 14 hours of culture at 0.3 vvm, 450 rpm, and 28° C.

Subsequently, cells were collected by centrifugation from the culture solution, suspended in N buffer (0.01% 2-mercaptoethanol, 0.1 mM phenyl methylsulfonyl fluoride (PMSF), 0.5 mM pyridoxal phosphate, 0.01 M potassium phosphate (pH8.0)), and then disrupted by ultrasonication. Solid matter in the disrupted product was removed by centrifugation, so that a cell-free extract was prepared.

The thus obtained cell-free extract was stirred at 50° C. for 30 minutes, the supernatant was collected by centrifugation, and then ammonium sulfate was added to a saturation of 30% and dissolved. The resulting precipitate was removed by centrifugation. Moreover, ammonium sulfate was added to the supernatant to a saturation of 75% and dissolved in the supernatant. The resulting precipitate was collected by centrifugation.

The precipitate was dissolved in N buffer and then dialysis was performed against the N buffer. The resultant was applied to a DEAE-TOYOPEARL 650 M (TOSOH CORPORATION) column (300 mL) equilibrated with the same buffer, so that an active fraction was adsorbed. The column was washed with the same buffer, and then the active fraction was eluted with a linear gradient (0 M to 0.45 M) of sodium chloride.

The thus eluted active fraction was collected. Sodium sulfate was dissolved in the fraction to a final concentration of 0.8 M. The solution was applied to a Butyl-TOYOPEARL 650S (TOSOH CORPORATION) column (120 mL) equilibrated in advance with 0.8 M sodium sulfate-containing N buffer, so that an active fraction was adsorbed. The column was washed with the same buffer, and then the active fraction was eluted with a linear gradient (0.8 M to 0.24 M) of sodium sulfate. The active fraction was collected and then concentrated by ultrafiltration (Centriplus YM-10).

The thus concentrated crude polypeptide solution was applied to a Hi LOAD 16/60 Superdex 200 p/g column (Amersham Biosciences K.K.) equilibrated in advance with N buffer to which 0.15 M sodium chloride had been added, so that an electrophoretically single purified polypeptide preparation was obtained. Furthermore, the molecular weight of the thus obtained purified polypeptide was about 50,000 as measured by SDS-polyacrylamide gel electrophoresis. Hereinafter, the polypeptide is referred to as "TPM."

Example 3

Cloning of TPM Gene (Preparation of PCR Primers)

The N-terminal amino acid sequence of purified TPM obtained in Example 2 was determined using a PPSQ-33A protein sequencer (Shimadzu Corporation). Moreover, the purified TPM obtained above was altered in the presence of 8 M urea and then the resultant was digested with *Achromobacter*-derived lysyl endopeptidase (Wako Pure Chemical Industries, Ltd.). The N-terminal amino acid sequence of the thus obtained peptide fragment was determined in a similar manner. The nucleotide sequence was predicted from the amino acid sequence and then primer 1 (SEQ ID NO: 3 in the sequence listing), and, primer 2 (SEQ ID NO: 4 in the sequence listing) were synthesized for amplification of a portion of the TPM gene by PCR.

(Amplification of TPM Gene by PCR)

Chromosomal DNA was extracted from the culture solution of the *Pseudomonas* sp. MV37 according to the method of Murray et al., (Nucl. Acids Res., 8, 4321, 1980). PCR was performed using the thus obtained chromosomal DNA as a template and the above-synthesized primers. As a result, an about 830-bp DNA fragment thought to be a portion of the TPM gene was obtained. PCR was performed under reaction conditions specified in the instruction manual using PrimeStar (Takara Bio Inc.) as DNA polymerase. The nucleotide sequence of the DNA fragment was determined by direct sequencing. The nucleotide sequence is shown in SEQ ID NO: 5 in the sequence listing.

(Determination of the Full-Length TPM Gene Sequence by Inverse-PCR Method)

The chromosomal DNA of *Pseudomonas* sp. MV37 was completely digested with a restriction enzyme (Fba I, Pst I, Xho I or Sph I). The thus obtained digests were each intramolecularly cyclized using T4 DNA ligase (Takara Shuzo Co., Ltd.). With the use of the resultant as a template, the full nucleotide sequence of the TPM gene on the chromosomal DNA was determined by the inverse-PCR method based on the above-found partial nucleotide sequence information of the TPM gene (Nucl. Acids Res., 16, 8186 (1988)). PCR was performed using TaKaRa LA Taq with GC buffer (Takara Shuzo Co., Ltd.) under reaction conditions specified in the instruction manual. The thus determined nucleotide sequence is shown in SEQ ID NO: 2 in the sequence listing. Also, the amino acid sequence encoded by the nucleotide sequence is shown in SEQ ID NO: 1 in the sequence listing.

Example 4

Construction of Recombinant Plasmid Containing TPM Gene

Based on the nucleotide sequence determined in Example 3, primer 3 (SEQ ID NO: 6 in the sequence listing) was synthesized by adding a Nde I site to the initiation codon of the TPM gene and primer 4 (SEQ ID NO: 7 in the sequence listing) was synthesized by adding a Sac I site so that it immediately followed the termination codon of the TPM gene. PCR was performed using the chromosomal DNA of *Pseudomonas* sp. MV37 obtained in Example 3 as a template and these primers. Thus, double-stranded DNA containing the Nde I site added to the initiation codon of the TPM gene and the Sac I site added so that it immediately followed the termination codon was obtained. PCR was performed under reaction conditions specified in the instruction manual using a PrimeSTAR (Takara Bio Inc.). The DNA was digested with Nde I and Sac I and then the digest was inserted between the Nde I recognition site and the Sac I recognition site downstream of an lac promoter of plasmid pUCNT (WO94/03613), so that a pNTTPM recombinant vector was obtained.

Example 5

Preparation of Recombinant *Escherichia coli*

*E. coli* HB101 (Takara Bio Inc.) was transformed with the pNTTPM recombinant vector obtained in Example 4, and thus recombinant *E. coli* HB101 (pNTTPM) was obtained.

Example 6

Expression of TPM Gene Using Recombinant *Escherichia coli*

The *E. coli* HB101 (pNTTPM) obtained in Example 5 was cultured in 2× YT media (triptone 1.6%, yeast extract 1.0%, NaCl 0.5%, pH7.0) containing 200 µg/ml ampicillin. After cells were collected, each resultant was suspended in N buffer and then subjected to ultrasonication, so that a cell-free extract was obtained. The cell-free extract was added to a substrate solution with the composition given below. After 1 hour of reaction at 30° C., 50 µL of 6 N hydrochloric acid was added to 1 mL of the reaction solution and then subjected to centrifugation. The acetophenone concentration of the thus obtained supernatant was determined by HPLC, and thus transamination activity was determined. As a result, *E. coli* HB101 (pNTTPM) cell-free extract was observed to have activity of generating 9 µmol acetophenone per minute and per mL of broth.

[Composition of Substrate Solution]

| | |
|---|---|
| (S)-1-phenethylamine | 25 mM |
| Sodium pyruvate | 25 mM |
| Pyridoxal phosphate | 2.5 mM |
| Tris-hydrochloride buffer (pH 8.0) | 0.1M |

[High Performance Liquid Chromatography (HPLC) Analysis Conditions]
Column: Cosmosil 5C8-MS (NACALAI TESQUE, INC.)
Eluent: 30 mM potassium phosphate buffer (pH2.5)/acetonitrile/methanol=4/1/1 (volume ratio)
Flow rate: 1 mL/minute
Detection: 254 nm Example 7

Purified TPM Preparation 2

Cells were collected by centrifugation from the recombinant *Escherichia coli* culture solution obtained by a method similar to that in Example 6. Cells were suspended in standard buffer (0.5 mM pyridoxal phosphate, 0.1 M potassium phosphate (pH 7.5)) and then disrupted by ultrasonication. Next, solid matter in the disrupted product was removed by centrifugation and then a cell-free extract was prepared. The thus obtained cell-free extract was treated at 50° C. while stirring for 30 minutes. The supernatant was collected by centrifugation.

The supernatant was applied to a DEAE-Sephacel column (GE HEALTHCARE BIO-SCIENCES) equilibrated with standard buffer, so that an active fraction was adsorbed. The column was washed with standard buffer containing 0.1 M sodium chloride, and then the active fraction was eluted with N buffer containing 0.2 M sodium chloride.

The thus eluted active fraction was collected and then sodium sulfate was dissolved in the resultant to a final concentration of 1.0 M. The solution was applied to a Butyl-TOYOPEARL 650 M (TOSOH CORPORATION) column equilibrated in advance with standard buffer containing 1.0 M sodium sulfate, so that an active fraction was adsorbed. The column was washed with standard buffer containing 0.8 M sodium sulfate, and then the active fraction was eluted with the same buffer containing 0.5 M sodium sulfate. The active fraction was collected and then dialyzed against standard buffer, so that an electrophoretically single purified TPM was obtained. The physico-chemical properties of the purified TPM (polypeptide) were examined.

Example 8

Purified TPM Physico-Chemical Properties 1

The purified TPM obtained in Example 7 was examined to determine its activity for 1-benzyl-3-pyrrolidinone and the optical purity of the generated (S)-1-benzyl-3-aminopyrrolidine.

The purified TPM obtained in Example 7 was added to the substrate solution with the composition given below. After 2 hours of reaction at 30° C., HPLC analysis was conducted under the following conditions. As a result, (S)-1-benzyl-3-aminopyrrolidine was generated with a conversion rate of 90%, and the optical purity was 98.0% e.e.

[Composition of Substrate Solution]

| (S)-1-phenethylamine | 85.6 mM |
| 1-benzyl-3-pyrrolidinone | 57.1 mM |
| Pyridoxal phosphate | 0.5 mM |
| Potassium phosphate buffer (pH 7.0) | 0.1M |

[High Performance Liquid Chromatography (HPLC) Analysis Conditions]
<Quantitative A>
Column: Finepak SIL C18-T (JASCO Corporation)
Eluent: distilled water 1260 mL/acetonitrile 740 mL/$KH_2PO_4$ 10 g/SDS 2.88 g (pH3.6)
Flow rate: 1 mL/minute
Detection: 254 nm
Column temperature: 40° C.
[Conditions for Optical Purity Analysis by High Performance Liquid Chromatography (HPLC)]
A reaction solution was treated with an appropriate amount of sodium carbonate so that it became basic, derivatized with dinitrobenzoyl chloride, and then analyzed under the following conditions.

Column: Chiral pak IA (Daicel Corporation)
Eluent: hexane/ethanol/diethylamine/acetonitrile=800/200/1/5 (volume ratio)
Flow rate: 0.8 mL/minute
Detection: 254 nm Example 9

Purified TPM Physico-Chemical Properties 2

The purified TPM obtained in Example 7 was examined to determine its activity for (S)-1-phenethylamine, optimum pH, optimum temperature, thermal stability, and resistance to a water-soluble organic solvent.

The transamination activity of purified TPM was examined under the following activity assay conditions. Specifically, purified TPM was added to a substrate solution with the composition given below to a total amount of 1 mL. After 5 minutes of reaction at 30° C., 0.05 mL of 6N hydrochloric acid was added to stop the reaction. HPLC analysis was conducted under the following conditions.

[Composition of Substrate Solution]

| (S)-1-phenethylamine | 25 mM |
| Sodium pyrubate | 25 mM |
| Pyridoxal phosphate | 2.5 mM |
| Tris-hydrochloride buffer (pH 8.0) | 0.1M |

[High Performance Liquid Chromatography (HPLC) Analysis Conditions]
Column: Wakosil-II 5C18 RS (Wako Pure Chemical Industries, Ltd.)
Eluent: 10 mM potassium phosphate buffer (pH5.3): acetonitrile=3:2
Flow rate: 1 mL/minute
Detection: 241 nm
(1) Activity for (S)-1-phenethylamine:
Trans amination activity was determined by the above method, so that purified TPM was found to have activity of 11.8 U/mg.
(2) Optimum pH:
Transamination activity was determined in a manner similar to the above at pHs ranging from 4.0 to 9.0 and then the optimum pH of TPM was examined.

The following buffers were used according to pH for determination. As a result, in the case of 0.1 M potassium phosphate buffer, the highest activity was exhibited at pH7.0 and the optimum pH was considered to range from 6.0 to 8.5 (Table 1 shows relative activity when the activity at pH7 was designated as 100).

TABLE 1

| Buffer type | pH | Relative activity |
|---|---|---|
| 0.1M Sodium acetate | 4.0 | 7 |
| | 4.5 | 25 |
| | 5.0 | 57 |
| | 5.5 | 71 |
| 0.1M Potassium phosphate | 6.0 | 86 |
| | 6.5 | 94 |
| | 7.0 | 100 |
| | 7.5 | 88 |
| | 8.0 | 67 |
| 0.1M Tris-hydrochloric acid | 7.5 | 96 |
| | 8.0 | 95 |
| | 8.5 | 85 |
| | 9.0 | 67 |

[Buffer]

pH4.0, 4.5, 5.0, or 5.5: 0.1 M sodium acetate buffer pH6.0, 6.5, 7.0, 7.5, or 8.0: 0.1 M potassium phosphate buffer pH7.5, 8.0, 8.5, or 9.0: 0.1 M tris-hydrochloric acid buffer (3) Optimum Temperature:

Transamination activity was determined at 10° C., 20° C., 30° C., 40° C., 50° C., 60° C., and 70° C. under the same conditions above. As a result, 60° C. was considered to be the optimum temperature for TPM (Table 2 shows relative activity when the activity at 60° C. was the highest and was designated as 100).

TABLE 2

| Reaction temperature (° C.) | Relative activity |
| --- | --- |
| 10 | 8 |
| 20 | 16 |
| 30 | 33 |
| 40 | 49 |
| 50 | 77 |
| 60 | 100 |
| 70 | 68 |

(4) Thermal Stability:

The purified TPM was reacted for 30 minutes in 0.1 M potassium phosphate buffer (pH7.5) containing 0.5 mM pyridoxal phosphate at 30° C., 40° C., 50° C., 60° C., 70° C., and 80° C., and then activity assay was performed in a similar manner. As a result, 90% or more of the activity before heat treatment remained after treatment at 30° C. to 60° C. (Table 3 shows residual activity when the activity before heat treatment was designated as 100.)

TABLE 3

| Temperature for treatment (° C.) | Residual activity |
| --- | --- |
| 30 | 108 |
| 40 | 115 |
| 50 | 120 |
| 60 | 100 |
| 70 | 12 |

(5) Resistance to water-soluble organic solvent: 800 µL of 1-propanol, 2-propanol, or acetone was added to 200 µL of 0.1 M potassium phosphate buffer (pH7.5) containing 0.5 mM pyridoxal phosphate to which purified TPM had been added, followed by 2 hours of treatment at 30° C. After treatment, 0.1 M potassium phosphate buffer (pH7.5) containing 0.5 mM pyridoxal phosphate was diluted 20-fold, and then the activity of the diluted solution was determined under conditions similar to those above. As a result, TPM was extremely stable against 1-propanol, 2-propanol, and acetone (Table 4).

TABLE 4

| Solvent | Residual activity rate (%) |
| --- | --- |
| Before treatment | 100 |
| 1-Propanol | 97 |
| 2-Propanol | 100 |
| Acetone | 99 |

Comparative Example 1

Resistance of Commercially Available Transaminase to Water-Soluble Organic Solvent The resistance of commercially available *Vibrio fluvialis*-derived ω-Transaminase VF (Julich-Chemicals) to a water-soluble organic solvent was examined by a method similar to that for resistance to a water-soluble organic solvent in Example 9 (5). As a result, the addition of 80% v/v 1-propanol, 2-propanol, or acetone resulted in complete loss of the activity within 2 hours (Table 5).

TABLE 5

| Solvent | Residual activity rate (%) |
| --- | --- |
| Before treatment | 100 |
| 1-Propanol | 0 |
| 2-Propanol | 0 |
| Acetone | 0 |

Example 10

Purified TPM Physico-Chemical Properties 3: Specificity to Amino Group Donor

The purified TPM obtained in Example 7 was examined to determine its specificity to amino group donors. First, 20 µL of a purified TPM solution was added to 380 µL of a substrate solution with the composition given below. After 1 hour of reaction at 30° C., 20 µL, of 3 N hydrochloric acid was added to stop the reaction. Next, 80 µl of an aqueous 0.2 M sodium carbonate solution and 200 µl of an acetone solution of 3.3 mg/mL Dabsyl chloride were added to 20 µL, of the thus obtained reaction solution, followed by 10 minutes of reaction at 70° C. 20 µL of acetic acid was added to the reaction solution. The reaction solution was stirred and then analyzed by HPLC under the following conditions, and thus the quantity of dabsylated alanine was determined. As a result, it was revealed that TPM exhibits its activity also for n-butylamine, benzylamine, or ±2-butylamine. (Table 6 shows relative activity when the activity obtained with the use of n-butylamine as an amino group donor was designated as 100%.)

[Composition of Substrate Solution]

| Various amino compounds | 14 mM (28 mM in the case of racemic body) |
| --- | --- |
| Pyruvic acid | 14 mM |
| Pyridoxal phosphate | 0.5 mM |
| Potassium phosphate buffer (pH 7.5) | 0.1M |

[High Performance Liquid Chromatography (HPLC) Analysis Conditions]

Column: Deverosil ODS-HG-3 (NOMURA CHEMICAL)

Eluent: acetonitrile/0.045 M acetate buffer (pH4.1)=35/65 (volume ratio)

Flow rate: 0.9 mL/minute

Detection: 254 nm

TABLE 6

| Amino group donor | Relative activity (%) |
| --- | --- |
| n-butylamine | 100% |
| benzylamine | 95% |
| ±2-butylamine | 67% |

Example 11

Purified TPM Physico-Chemical Properties 4: Specificity 2 to Amino Group Donor The purified TPM obtained in Example 7 was examined to determine its reactivity to typical substrates of ω-amino acid transaminase. First, 20 μL of a purified TPM solution was added to 380 μL of a substrate solution with the composition given below. After 1 hour of reaction at 30° C., 20 μL of 3 N hydrochloric acid was added to stop the reaction. Next, 80 μL of a 0.2 M aqueous sodium carbonate solution and 200 μL of an acetone solution of 3.3 mg/mL Dabsyl chloride were separately added to 20 μL of the thus obtained reaction solution, followed by 10 minutes of reaction at 70° C. 20 μL of acetic acid was added to the solution and then it was stirred. The reaction solution was analyzed by HPLC under the following conditions, and thus the quantity of dabsylated alanine was determined. As a result, it was revealed that TPM does not exhibit activity for β-alanine, 4-aminobutyric acid, L-ornithine, L-lysine, putrescine, and taurine, which are typical substrates of ω-amino acid transaminase. (Table 7 shows relative activity when the activity obtained with the use of (S)-1-phenethylamine as an amino group donor was designated as 100.).

[Composition of Substrate Solution]

| Various amino compounds | 14 mM |
|---|---|
| Pyruvic acid | 14 mM |
| Pyridoxal phosphate | 0.02 mM |
| Potassium phosphate buffer (pH 7.5) | 0.1M |

[High Performance Liquid Chromatography (HPLC) Analysis Conditions]
Column: Deverosil ODS-HG-3 (NOMURA CHEMICAL)
Eluent: acetonitrile/0.045 M acetate buffer (pH4.1)=35/65 (volume ratio)
Flow rate: 0.9 mL/minute
Detection: 254 nm

TABLE 7

| Amino group donor | Relative activity (%) |
|---|---|
| (S)-α-phenethylamine | 100 |
| β-alanine | 0 |
| 4-aminobutyric acid | 0 |
| L-ornithine | 0 |
| L-lysine | 0 |
| Putrescine | 0 |
| Taurine | 0 |

Example 12

Purified TPM Physico-Chemical Properties 5: Specificity to Amino Group Receptor The purified TPM obtained in Example 7 was examined to determine the substrate specificity to amino group receptors. A substrate solution was added to the purified TPM solution, so that the final concentrations of the components would be as follows. After 5 minutes of reaction at 30° C., 6N hydrochloric acid was added in an amount of 50 μL per mL of the reaction solution, so as to stop the reaction. The reaction solution was analyzed by HPLC under the following conditions. It was revealed that TPM exhibits activity for a wide variety of substrates (Table 8).

[Composition of Substrate Solution]

| (S)-1-phenethylamine | 25 mM |
|---|---|
| Each amino group receptor | 25 mM or 2.5 mM |
| Pyridoxal phosphate | 2.5 mM |
| Tris-hydrochloride buffer (pH 7.0) | 0.1M |
| Polypeptide solution | |

[High Performance Liquid Chromatography (HPLC) Analysis Conditions]
Column: Wakosil-II 5C18 RS (Wako Pure Chemical Industries, Ltd.)
Eluent: 10 mM potassium phosphate buffer (pH5.3): acetonitrile=3:2
Flow rate: 1 mL/minute
Detection: 241 nm

TABLE 8

| Amino group receptor | Substrate concentration | Relative activity (%) |
|---|---|---|
| Pyruvic acid | 25 mM | 100 |
| 2-ketoglutaric acid | 25 mM | 0 |
| Glyoxalic acid | 25 mM | 40 |
| Butylaldehyde | 2.5 mM | 7 |
| Benzaldehyde | 2.5 mM | 149 |
| 2-heptanone | 2.5 mM | 4.6 |
| Benzyl phenyl ketone | 2.5 mM | 3.8 |
| 2-acetylpyridine | 2.5 mM | 16 |
| Acetylpyrazine | 2.5 mM | 23 |
| Benzylacetone | 2.5 mM | 12 |
| Benzoylacetic acid ethyl | 2.5 mM | 13 |
| 2-tetralone | 2.5 mM | 17 |
| 1-benzyl-3-pyrrolidinone | 2.5 mM | 4.7 |

Example 13

Production of Optically Active 1-benzyl-3-aminopyrrolidine by Production Method I The culture solution of recombinant *Escherichia coli* obtained by a method similar to that in Example 6 was subjected to centrifugation, so that cells were collected. Furthermore, recombinant *Escherichia coli* coexpressing *Pediococcus acidilactici* JCM8797 strain-derived L-lactate dehydrogenase PALDH and *Bacillus megaterium* IAM1030-derived glucose dehydrogenase GDH described in Example 13 of WO2007/139055 was cultured in 2× YT medium (triptone 1.6%, yeast extract 1.0%, NaCl 0.5%, pH7.0) containing 200 μg/ml ampicillin, and then cells were collected by centrifugation.

The above culture solutions were mixed to become TPM (15.8 U/mL), PALDH (380 U/mL), and GDH (41 U/mL). 3 ml of the above cell suspension, 4 mg of pyridoxal phosphate, and 3 mL of 1 M potassium phosphate buffer (pH6.8) were added to a flask containing 900 mg of 1-benzyl-3-pyrrolidinone as a substrate, 3730 mg of L-alanine, 1390 mg of D-glucose, and 4 mg of NAD+ added in advance. Deionized water was added to the resultant so that the total volume is 30 mL. The solution was adjusted with sodium hydroxide to pH6.8 at 30° C. and then reaction was performed for 5 hours with stirring. After the completion of the reaction, the reaction solution was analyzed by HPLC under the following conditions. As a result, 1-benzyl-3-aminopyrrolidine was generated with a conversion rate of 100%, the configuration was found to be (S) configuration, and the optical purity was 98.3% e.e.

[High Performance Liquid Chromatography (HPLC) Quantitative Analysis Conditions]
<Quantitative Analysis>
Column: Finepak SIL C18-T (JASCO Corporation)
Eluent: distilled water 1260 mL/acetonitrile 740 mL/KH$_2$PO$_4$ 10 g/SDS 2.88 g (pH3.6)
Flow rate: 1 mL/minute
Detection: 254 nm
Column temperature: 40° C.
[Conditions for Optical Purity Analysis by High Performance Liquid Chromatography (HPLC)]
A reaction solution was treated with an appropriate amount of sodium carbonate so that it became basic, derivatized with dinitrobenzoyl chloride, and then analyzed under the following conditions.
Column: Chiralcel IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

Example 14

Production of Optically Active 2-aminoheptane by Production Method I

TPM, PALDH, and GDH obtained by a method similar to that in Example 13 were mixed so that the culture solution contained 16.7 U/mL TPM, 297 U/mL PALDH, and 30 U/mL GDH. 3 ml of the above cell suspension, 1.3 mg of pyridoxal phosphate, and 1 mL of 1 M potassium phosphate buffer (pH6.8) were added to a flask containing 300 mg of 2-heptanone as a substrate, 15900 mg of L-alanine, 710 mg of D-glucose, and 4 mg of NAD+ added in advance thereto. Deionized water was added to the resultant to the total volume of 10 mL. The solution was adjusted to pH6.8 with sodium hydroxide at 30° C. and then reaction was performed for 30 hours with stirring. After the completion of the reaction, the reaction solution was analyzed by HPLC under the following conditions. As a result, 2-aminoheptane was generated with a conversion rate of 99%, the configuration was found to be (S) configuration, and the optical purity was 99.2% e.e.

[Gas Chromatography (GC) Quantitative Analysis Conditions]
Column: Rtx-5 Amine (30 m, 0.25 mmID) (RESTEK)
Column temperature: 50° C.
Injection port temperature: 250° C.
Detector temperature: 220° C.
Detection: FID
Carrier gas: He, 150 kPa
Conditions for Optical Purity Analysis by High Performance Liquid Chromatography (HPLC)
A reaction solution was treated with an appropriate amount of sodium carbonate so that it became basic, derivatized with dinitrobenzoyl chloride, and then analyzed under the following conditions.
Column: Chiralpak AD-H (Daicel Corporation)
Eluent: n-hexane/ethanol/diethylamine=90/10/0.1 (volume ratio)
Flow rate: 1.0 mL/minute
Detection: 240 nm
Column temperature: 35° C.

All publications, patents, and patent applications cited herein are incorporated herein by reference in their entirety.

The invention claimed is:

1. A DNA consisting of a nucleotide sequence encoding a polypeptide selected from the group consisting of:
   (a) a polypeptide consisting of an amino acid sequence that is identical to the amino acid sequence of SEQ ID NO: 1 except for a deletion, a substitution, an insertion and/or an addition of 1 to 20 amino acids in SEQ ID NO: 1, wherein said polypeptide acts on 1-benzyl-3-pyrrolidinone in the presence of an amino group donor to generate (S)-1-benzyl-3-aminopyrrolidine with optical purity of 93% enantiomeric excess or more; and
   (b) a polypeptide consisting of an amino acid sequence that is identical to the amino acid sequence of SEQ ID NO: 1 except for a deletion, a substitution, an insertion and/or an addition of 1 to 20 amino acids in SEQ ID NO: 1, wherein said polypeptide acts on 1-benzyl-3-pyrrolidinone in the presence of an amino group donor to generate (S)-1-benzyl-3-aminopyrrolidine with optical purity of 93% enantiomeric excess or more; and wherein said polypeptide (i) exhibits activity for (S)-1-phenethylamine, benzylamine, and 2-butylamine as amino group donors and does not substantially exhibit activity for β-alanine and 4-aminobutyric acid, (ii) exhibits activity for pyruvic acid and activity for glyoxalic acid as amino group receptors; and/or (iii) retains 10% or more of residual activity after 2 hours of treatment with a solution having a concentration of 80% v/v of 1-propanol, 2-propanol, or acetone compared to the enzymatic activity prior to the treatment.

2. A vector comprising a DNA consisting of a nucleotide sequence encoding a polypeptide selected from the group consisting of:
   (a) a polypeptide consisting of the amino acid sequence of SEQ ID NO: 1;
   (b) a polypeptide consisting of an amino acid sequence that is identical to the amino acid sequence of SEQ ID NO: 1 except for a deletion, a substitution, an insertion and/or an addition of 1 to 20 amino acids in SEQ ID NO: 1, wherein said polypeptide acts on 1-benzyl-3-pyrrolidinone in the presence of an amino group donor to generate (S)-1-benzyl-3-aminopyrrolidine with optical purity of 93% enantiomeric excess or more;
   (c) a polypeptide consisting of an amino acid sequence which is at least 95% identical to SEQ ID NO: 1, wherein said polypeptide acts on 1-benzyl-3-pyrrolidinone in the presence of an amino group donor to generate (S)-1-benzyl-3-aminopyrrolidine with optical purity of 93% enantiomeric excess or more; and (d) a polypeptide consisting of an amino acid sequence which is at least 95% sequence identical to SEQ ID NO: 1, wherein said polypeptide acts on 1-benzyl-3-pyrrolidinone in the presence of an amino group donor to generate (S)-1-benzyl-3-aminopyrrolidine with optical purity of 93% enantiomeric excess or more; and wherein said polypeptide (i) exhibits activity for (S)-1-phenethylamine, benzylamine, and 2-butylamine as amino group donors and does not substantially exhibit activity for β-alanine and 4-aminobutyric acid, (ii) exhibits activity for pyruvic acid and activity for glyoxalic acid as amino group receptors; and/or (iii) retains 10% or more of residual activity after 2 hours of treatment with a solution having a concentration of 80% v/v of 1-propanol, 2-propanol, or acetone compared to the enzymatic activity prior to the treatment.

3. A transformant which is obtained by transformation of a host cell with the Vector of claim 2.

4. A method for producing an optically active amino compound, wherein said method comprises contacting the transformant of claim 3 with a ketone compound in the presence of an amino group donor, wherein said ketone comprises formula (1)

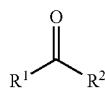

(1)

wherein $R^1$ and $R^2$ are (a) alkyl groups that may be substituted, aralkyl groups that may be substituted, or aryl groups that may be substituted, wherein $R^1$ and $R^2$ are different, or (b) linked to form a ring, and wherein the optically active amino compound comprises formula (2)

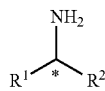

(2)

wherein $R^1$ and $R^2$ are as defined in formula (1) as set forth above, and wherein "*" denotes an asymmetric carbon atom.

5. The method of claim 4, wherein the ketone compound comprising formula (1) is selected from the group consisting of 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, and 3,4-dimethoxyphenyl acetone.

6. The method of claim 4, wherein the amino group donor is selected from the group consisting of 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, 3-amino-l-phenylbutane, benzylamine, .beta.-phenethylamine, and cyclohexylamine.

7. A method for producing an optically active amino compound, wherein said method comprises contacting the transformant of claim 3 with an enantiomeric mixture of amino compounds in the presence of an amino group receptor, wherein said amino compounds comprise formula (3)

(3)

wherein $R^1$ and $R^2$ are (a) alkyl groups that may be substituted, aralkyl groups that may be substituted, or aryl groups that may be substituted, wherein $R^1$ and $R^2$ are different, or (b) linked to form a ring, and wherein the optically active amino compound comprises formula (2)

(2)

wherein $R^1$ and $R^2$ are as defined in formula (3) as set forth above, and wherein "*" denotes an asymmetric carbon atom.

8. The method of claim 7, wherein the amino compounds comprising formula (3) are selected from the group consisting of 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, and 3,4-dimethoxyamphetamine.

9. The method of claim 7, wherein the amino group receptor is pyruvic acid or glyoxalic acid.

* * * * *